US00PP09029P

United States Patent [19]

Mantel

[11] Patent Number: Plant 9,029

[45] Date of Patent: Jan. 3, 1995

[54] LILIUM 'GOLD DWARF'

[76] Inventor: Homme Mantel, 15361 S.E. Bluff Rd., Sandy, Oreg. 97055

[21] Appl. No.: 238,028

[22] Filed: May 4, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing large upright-facing flowers of excellent form and long persistence. The new hybrid is particularly characterized by its short stature and its lightly spotted golden flowers with deeper gold-orange midribs. This combination is competely new in the Asiatic hybrid divisions of lilies suited to forcing and to mass commercial cultivation. The variety is highly resistant to fusarium disease and shows tolerance of virus. The bulbs may be precooled and forced into flower under glass out of season. The clone is vigorous and is a good grower and propagator.

1 Drawing Sheet

BACKGROUND OF THE INVENTION

My new variety of lily plant originated as a seedling, which first flowered in't Zand, Netherlands in 1986. The breeding efforts had as their objective the production of truly short Asiatic hybrid lilies with upfacing, vibrant yellow and gold flowers, suited to forcing into flower out of season for use as pot plants, heretofore unknown in the lily breeding art.

I achieved the desired objective by intercrossing *Lilium* 'Charisma' (U.S. Plant Pat. No. 4,180) with *Lilium* 'Sunray.' 'Sunray,' one of the early Stone and Payne hybrids from Connecticut, has been grown in the Netherlands and in the United States as a commercial cut-flower and pot-plant; it is too tall for an ideal pot-plant, however, and its more outfacing yellow flowers are not large. The flowers of my new lily are characterized by brilliant gold color with a deeper golden-orange margin, light spotting in the center only, and large size. The clone possesses unusually short, strong, stout stems. In addition, it possesses to a high degree desirable characteristics of hybrid vigor. The clone is a good grower and propagator, as observed at't Zand, Netherlands.

My new variety of lily plant has been asexually reproduced by me and under my direction at't Zand, Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawings, which show the open bloom in full color and illustrate the flower form, the tepal arrangement, and in particular the novel and distinctive lightly spotted, brilliant gold flowers with golden-orange margins, borne on a short, sturdy stem.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

THE PLANT

Origin: Seedling.

*Seed parent.*—*Lilium* 'Charisma' (U.S. Plant Pat. No. 4,180).

*Pollen parent.*—*Lilium* 'Sunray'.

Commercial classification: Hybrid *Lilium* clone.

Horticultural classification: Division IA, Upright Asiatic hybrid lily, according to the Horticultural Classification of Lilies, Royal Horticultural Society of London.

Form: Single stem, erect and stately.

Height: 20 to 45 cm from bulbs 14 to 18 cm in circumference, provided their light levels are adequate; low light levels may cause "stretching."

Growth: Vigorous and upright.

Foliage quantity: Abundant.

Size of leaf: 8 to 12 cm long ×1.5–2.5 cm wide.

Shape of leaf: Lanceolate (pointed).

Texture: Leathery and glossy.

Color: Medium to dark green lighter on lower side.

Bulb:

*Size.*—Any size, ranging to 25 cm circumference commercially.

*Color.*—White, with flushes of pink or yellow after exposure to light.

THE BUD

Form: Obtuse, ovoid, and long.

Size: 7 to 9 cm long and 8 to 12 cm in circumference just prior to opening.

Opening: Bud opens slowly, in response to morning light; this takes about one hour.

Color: R.H.S. C.C. yellow-orange 23 C, slightly lighter at base and apex.

Peduncle: Averages 1 to 3 cm, but it may elongate if light levels are too low or if bulbs have been improperly stored prior to forcing. Color is deep green with a purple overlay, which is deepest under cultivation with bright light intensities.

THE FLOWER

Blooming habit: Annually in midseason; flowers once and profusely.

Size: Flowers are large-sized, averaging 15 to 17 cm in diameter, reflexing at the tips on the second day to 14 to 16 cm in diameter. The tepals are broad: outer tepals are 1.75 to 2.5 cm wide at the center, and the inner tepals are 2.25 to 3 cm wide at the center.

Borne: In a single compact racemic inflorescence producing 3 to 8 flowers from a bulb 14 to 16 cm in circumference. The raceme is so shortened that it appears to be an umbel, with all pedicels emerging from a single point. The inflorescence from larger bulbs has a compact racemose inflorescence.

Shape: Flowers from an open bowl with pointed, lightly recurved tepal tips by the second day after opening.

Tepalage: Typical of genus *Lilium,* with 6 imbricated tepals.

Tepal:

*Color.*—R.H.S. C.C. yellow-orange 14B/C to 16 A in an area averaging 1 cm wide along tepal midribs, shading to 25 A/B to 24 A/B along tepal margins, depending upon growing temperatures and light levels. Tepals will be lighter, less orange, and more gold, when grown with low light levels and high temperatures. The golden area along the tepal midribs will be wider with low light level and high temperatures; it will be narrower, and the golden-orange tepal edges will be wider, when light levels are high and temperatures are moderate. A narrow ray 1–2 mm wide of the same golden-orange as the tepal margins may also extend 1–2 cm from the nectaries when light levels are high and temperatures are moderate. With less ideal lighting, this deeper pigmentation will not appear.

*Spotting.*—The basal third of the inner tepals is lightly spotted with small, magenta-colored spots.

*Longevity.*—Tepals stay on stems about three weeks.

Pedicel:

*Length.*—Averages 3 to 7 cm long.

Color.—Dark green with plum overlay, which id deeper with bright illumination and paler at low light levels.

*From.*—Sturdy and somewhat ascending.

Color changes: Flowers become slightly more golden-yellow as the flowers age. Low light levels and extreme heat may cause a decrease in anthocyanin levels, making the color appear more golden yellow with hardly any golden-orange edge.

Appearance: Flower is shiny.

Disease resistance: The flower and plant are resistant to disease; in particular, they are resistant to Fusarium bulb rot and Botrytis blight.

Frangrance: None.

Lasting quality: The flower is long lasting.

THE REPRODUCTIVE ORGANS

Stamens: Arrangement typical of genus *Lilium.* Six stamens with soft gold (R.H.S. C.C. Yellow-orange 16 D) filaments 8 to 10 cm long.

Pollen and anthers (dehisced): R.H.S. C.C. greyed orange 171–172 A.

Pistil: One in number, 6 to 8 cm long, R.H.S. C.C. yellow-orange 16 C-D.

Stigma: Medium in size, soft grey and inconspicuous in coloring.

Characteristics of ovary: Characteristic of genus *Lilum.*

THE FRUIT

Fertility: The fruit bears fertile seed.

Shape: Ovoid.

Color at maturity: Soft brown, sometimes overlaid with soft plum.

My new variety of Asiatic hybrid lily most nearly resembles 'Charisma,' but is has flowers which are lightly spotted and which are more golden and less orange in color. Its stems are shorter than those of 'Charisma,' when grown from bulbs of the same size.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower from form, size and substance; its versatility both as a garden plant and as a pot plant produced from pre-cooled bulbs forced under glass out of season; and in particular by its lightly spotted golden flowers with golden-orange margins, borne in a compact inflorescence on extremely short stems, a combination unique among Asiatic hybrid lilies suited to forcing and to mass commercial cultivation.

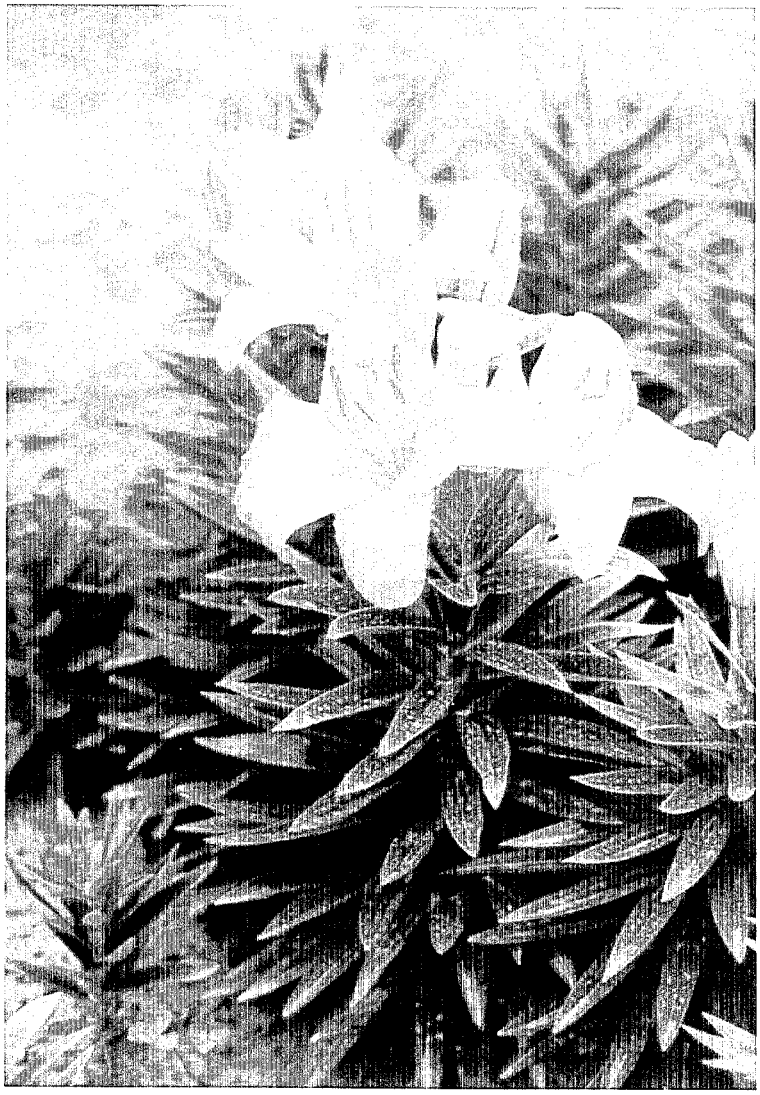
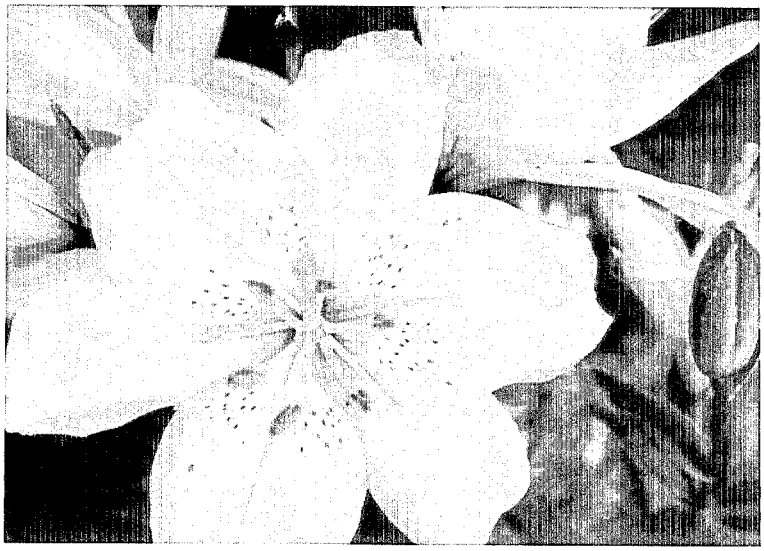

* * * * *